(12) United States Patent
Vukosavljevic et al.

(10) Patent No.: US 10,582,762 B2
(45) Date of Patent: Mar. 10, 2020

(54) INTERCHANGEABLE BRUSH HEAD WITH ULTRASOUND ACTION

(71) Applicants: Jovica Vukosavljevic, Karlsruhe (DE); Peer Blumenschein, Basel (CH)

(72) Inventors: Jovica Vukosavljevic, Karlsruhe (DE); Peer Blumenschein, Basel (CH)

(73) Assignees: Jovica Vukosavljevic, Karlsruhe (DE); Peer Blumenschein, Basel (CH)

( * ) Notice: Subject to any disclaimer, the term of this patent is extended or adjusted under 35 U.S.C. 154(b) by 167 days.

(21) Appl. No.: 15/752,958

(22) PCT Filed: Aug. 11, 2016

(86) PCT No.: PCT/DE2016/000315
§ 371 (c)(1),
(2) Date: Feb. 15, 2018

(87) PCT Pub. No.: WO2017/028835
PCT Pub. Date: Feb. 23, 2017

(65) Prior Publication Data
US 2018/0242723 A1 Aug. 30, 2018

(30) Foreign Application Priority Data
Aug. 18, 2015 (DE) .......................... 10 2015 010 483

(51) Int. Cl.
*A46B 7/04* (2006.01)
*A46B 15/00* (2006.01)
(Continued)

(52) U.S. Cl.
CPC ................ *A46B 7/04* (2013.01); *A46B 9/045* (2013.01); *A46B 15/0028* (2013.01); *A61C 17/20* (2013.01)

(58) Field of Classification Search
CPC ....... A46B 7/04; A46B 9/045; A46B 15/0028; A46B 2200/1066; A61C 17/20
See application file for complete search history.

(56) References Cited

U.S. PATENT DOCUMENTS 5,546,624 A  8/1996  Bock
7,849,548 B2  12/2010  Bock
(Continued)

FOREIGN PATENT DOCUMENTS

CA  2816604 A1  5/2012
CN  101 836 901 A  9/2010
(Continued)

OTHER PUBLICATIONS

International Search Report of PCT/DE2016/000315, dated Dec. 22, 2016.

*Primary Examiner* — Weilun Lo
(74) *Attorney, Agent, or Firm* — Collard & Roe, P.C.

(57) ABSTRACT

An interchangeable brush head with ultrasound action makes it possible by way of the thin wall, which has a wall thickness of equal to or less than a millimeter and a low damping coefficient, for the energy to be transmitted as directly as possible by the ultrasonic waves into the effective medium, whereby the otherwise very high losses in the case of such prior-art appliances of the type in question are largely avoided, wherein, at the same time, the safety-related and dental-care aspects and the user-friendliness are increased. Further advantageous measures for increasing the efficiency of transmission are also present. Certain embodiments have only a directly interchangeable insert with the bristles thereon, this being environmentally friendly, user-friendly and cost-saving. In other embodiments, the entire interchangeable brush head, together with the electromechanical transducer installed therein and the neck, has to be replaced.

20 Claims, 16 Drawing Sheets

(51) Int. Cl.
*A46B 9/04* (2006.01)
*A61C 17/20* (2006.01)

(56) References Cited

U.S. PATENT DOCUMENTS

| | | | |
|---|---|---|---|
| 8,931,129 B2 | 1/2015 | Emekei | |
| 2005/0050659 A1* | 3/2005 | Chan | A46B 15/0036 |
| | | | 15/22.1 |
| 2005/0091770 A1* | 5/2005 | Mourad | A46B 15/0002 |
| | | | 15/22.1 |
| 2008/0209650 A1* | 9/2008 | Brewer | A46B 15/0002 |
| | | | 15/22.1 |
| 2009/0211042 A1* | 8/2009 | Bock | A46B 13/023 |
| | | | 15/22.1 |
| 2010/0092916 A1* | 4/2010 | Teixeira | A61H 23/02 |
| | | | 433/103 |
| 2010/0237720 A1 | 9/2010 | Taylor | |
| 2013/0091642 A1* | 4/2013 | Dykes | A46B 15/0008 |
| | | | 15/22.1 |
| 2014/0310902 A1 | 10/2014 | Gerlach et al. | |
| 2015/0327964 A1* | 11/2015 | Bock | A46B 15/0028 |
| | | | 433/216 |

FOREIGN PATENT DOCUMENTS

| | | |
|---|---|---|
| DE | 10 2011 055564 A1 | 5/2013 |
| DE | 10 2012 021262 A1 | 5/2013 |
| EP | 1 681 956 B1 | 3/2009 |
| EP | 2 637 600 B1 | 1/2017 |
| JP | 2003-088426 A | 3/2003 |
| JP | 2005-066024 A | 3/2005 |
| JP | 2009-247800 A | 10/2009 |
| WO | 2009/108262 A4 | 9/2009 |
| WO | 2012/062277 A2 | 5/2012 |

\* cited by examiner

INTERCHANGEABLE BRUSH HEAD WITH ULTRASOUND ACTION

CROSS REFERENCE TO RELATED APPLICATIONS

This application is the National Stage of PCT/DE2016/000315 filed on Aug. 11, 2016, which claims priority under 35 U.S.C. § 119 of German Application No. 10 2015 010 483.7 filed on Aug. 18, 2015, the disclosure of which is incorporated by reference. The international application under PCT article 21(2) was not published in English.

The invention relates to an interchangeable brush head with ultrasound action for ultrasound devices, in particular for an ultrasound toothbrush and/or for an ultrasound therapy and massage device, in accordance with the preamble of claim 1.

Such interchangeable brush heads with ultrasound action or replacement brush heads for ultrasound toothbrushes, of the stated type, are known from U.S. Pat. No. 7,849,548 B2, for example, which is identical with WO 2009108262 A4.

In the case of such a replacement brush head, the electromechanical transducer or a piezo element has been firmly affixed in thee extension of the handle, and interacts with the interchangeable replacement insert that has the bristles, in such a manner that the active surface of the electromechanical transducer, i.e. of the piezo element, is situated very closely below the bristle tip plane; this does bring with it good conduction of the ultrasound into the effective medium, but demonstrates the significant disadvantage, in terms of safety technology and medicine, that the users can easily injure themselves on a hard material that is positioned so high up, or that during use, they constantly bump up against the teeth with this characteristic, which projects out very high, and/or rub or scratch against it or the like, and/or that the region of the piezo element can also easily break, since the users frequently also apply manual force even when using ultrasound brushes, and this is simply impossible to eliminate from practical use. This is evident from the cited document, there in FIGS. 1, 2, 4, and 5, also there in column 4, lines 6-9, and in claim 1 under d.). The engagement connection there is also very voluminous, very difficult and expensive to design and produce, wherein also very many more or less unstable contact surfaces bring further disadvantages with them as breeding grounds for bacteria.

JP 2005066024 A, in particular in FIGS. 1-2, also demonstrates the same disadvantages as described above.

EP 1681956 B1 also has a similar interchangeable brush head for an ultrasound toothbrush, in FIGS. 1-3 and there in claim 1, where a very high, voluminous, and round curvature of the active element (24)—there FIG. 1-2, is present, wherein adaptation layers (impedance adaptation layers), which can be produced only with great difficulty and at great expense, are provided, which layers are supposed to transport the ultrasound from a piezo element present in the brush head into the active medium.

Here, too, the great losses in ultrasound energy, ultrasound power, and ultrasound intensity brought about by very many and long connections/contact surfaces between the multiple, thick layers must be accepted. For the remainder, in this object the same further disadvantages are present as the disadvantages explained with regard to the above U.S. Pat. No. 7,849,548 B2.

US 20100237720 A1 also has an interchangeable brush head for an ultrasound toothbrush, where a piezo element (22, FIG. 1 there) is affixed in the brush head. However, there is no concrete information anywhere in the document with regard to placement or the concrete function of the same characteristic.

JP 2009247800 A, in FIGS. 1, 3, and 4, has a piezo element (12) present in the neck of the handle, where the transmission paths of the ultrasound energy from the ultrasound waves to the bristle tips (22) and an emission surface (21) are very long and complicated, wherein the energy losses are very high.

A conventionally operated ultrasound toothbrush is known from U.S. Pat. No. 5,546,624 and EP 2637600, which is identical with WO 2012062277 A2. A piezoelectric transducer is affixed directly above the attachment-side bristle region in these two devices, i.e. in their interchangeable brush heads.

In the case of such solutions, extremely high losses in ultrasound power and ultrasound intensity occur, specifically in the amount of more than 99.9%.

The company Emag AG from Germany has been having the object of the invention from WO 2012062277 A2 produced and sold internationally, specifically under the commercial name "Emmi Dental Professional."

The same ultrasound toothbrush "Emmi Dental Professional"—according to the invention here—was only able to achieve an average ultrasound intensity, I=0.0000124 watts per cm$^2$ (=0.0124 milliwatts per cm$^2$)—the respective peak value over the smallest area was I=0.0000312 watts per cm$^2$ (=0.0312 milliwatts per cm$^2$)—on Sep. 18, 2014, at TÜV SÜD Product Service GmbH,—Active Medical Products—Munich, Department of Ultrasound Medical Technology—in the ultrasound-acoustical measurements of the bristle field (at a distance of approximately 2 mm of the respective bristle tips from the tip of the measurement electrode of the needle hydrophone), using the officially calibrated and scientifically calibrated needle hydrophones of the English specialty company "Precision Acoustic," in a degassed and de-ionized water bath, at a temperature of 21.3° C. (everything according to the international testing guideline IEC60601-1 3, and with IEC 62304 Software Certification), and this in turn is also completely unsuitable for the formation of cavities and for implosions of the cavities in the cleaning medium, which in turn should clean the teeth and gums in abrasion-free manner.

The measured values therefore have a purely symbolic significance. It is known that the cavitation threshold lies significantly higher, in the frequency range from 280 Khz-1.7 MHz (ultrasound toothbrushes work in this frequency range), and can range from approximately 0.02 watts/cm$^2$ to approximately (more likely) 1.50 watts/cm$^2$, so that in the case of the ultrasound toothbrush "Emmi Dental Professional," this value was lower by 1,613 times to actually 121,000 times, and therefore it must be stated that the same ultrasound toothbrush (according to the invention) "Emmi Dental Professional" cannot clean the teeth and gums with ultrasound at all.

At the same time, upon the occasion of Sep. 18, 2014, two other commercial ultrasound toothbrushes were measured, which have the commercial names "Megasonex M8" and "Smilex," with the two toothbrushes having been designed and built according to U.S. Pat. No. 5,546,624 A.

For the last two ultrasound toothbrushes, it was not possible to measure any ultrasound intensity at all and any ultrasound power, since their losses are also simply extremely high, in spite of the very sensitive professional measurement instruments.

DE 102012021262 A1 has a triple-head ultrasound toothbrush. Here, too, one or more piezo elements are affixed directly subsequent to the attachment-side region of the bristles, and high losses of sonic power and sonic intensity occur here, too.

Accordingly, the invention is based on the task of at least reducing the disadvantages of the state of the art as described above, and simultaneously paying attention to the safety technology concerns of the users, with simultaneous and equivalent consideration of the required generation of ultrasound intensity and ultrasound power for the formation of cavitations and/or implosions in the effective cleaning medium, wherein the energy from the ultrasound waves is passed to the effective medium as directly as possible from a sound-emitting surface, while avoiding the extremely lossy conduction of the same energy from the ultrasound waves through the entire body of a brush head and through the bristles, if possible.

This task is accomplished, in the case of an interchangeable brush head with ultrasound action for ultrasound devices, in particular for an ultrasound toothbrush and/or for an ultrasound therapy and massage device, by means of the characterizing features of claim 1.

Advantageous further developments and embodiments of the interchangeable brush head with ultrasound action for ultrasound devices, in particular for an ultrasound toothbrush and/or for an ultrasound therapy and massage device, are indicated in the dependent claims.

Figure 1:
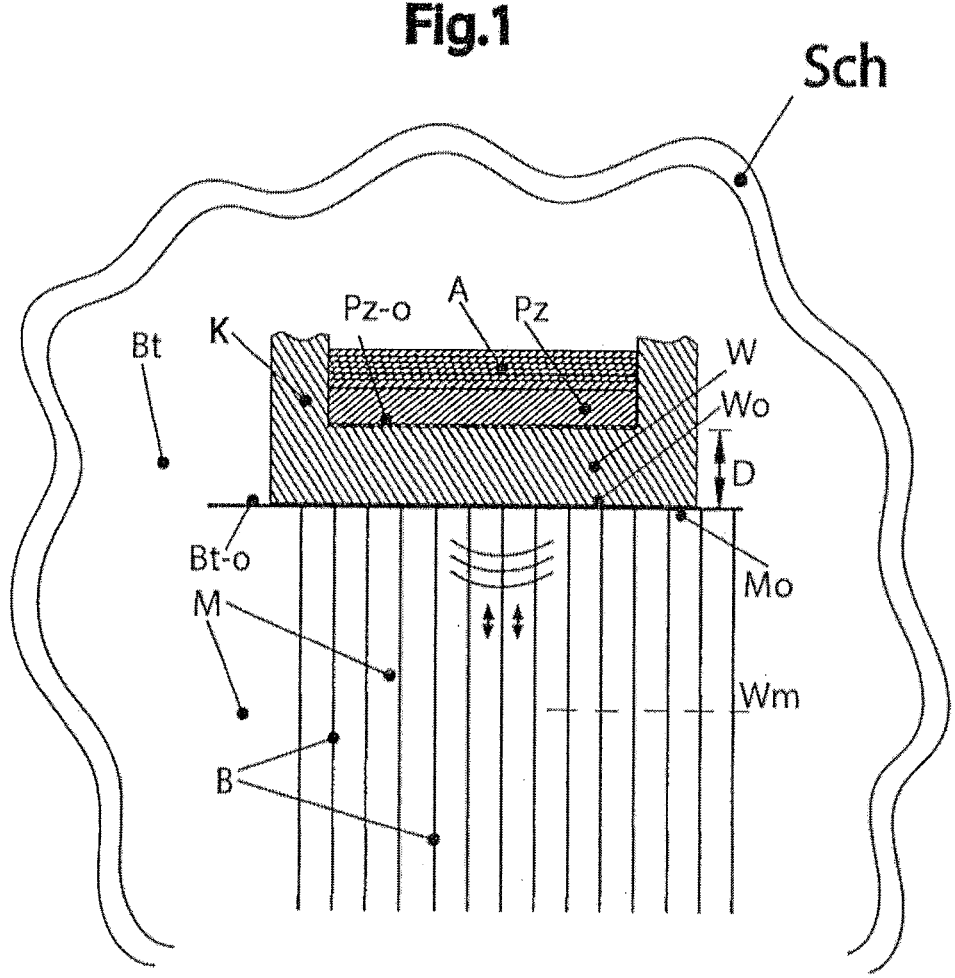
FIG. 1, in a frontal and/or side view, schematically shows the interchangeable brush head with ultrasound action for ultrasound devices, in particular for an ultrasound toothbrush and/or for an ultrasound therapy and massage device.

Exemplary embodiments of the invention are shown in FIG. 1 to FIG. 28, and will be described as follows, using the drawings:

FIG. 1, in a frontal and/or side view, schematically shows the interchangeable brush head with ultrasound action for ultrasound devices, in particular for an ultrasound toothbrush and/or for an ultrasound therapy and massage device, consisting of a basic element (Bt-o) that firmly carries the bristles (B), and a plurality or great number of bristles (B) affixed on its side that faces the effective medium (M), wherein the bristles (B) form a bristle field, wherein the same bristle field is situated in the spatial region of action of a sonic field (Sch), where it is evident that at least one electromechanical transducer (Pz) present in the sonic field (Sch), in particular a piezoelectric actuator or piezoelectric stack actuator, emits the energy produced by the ultrasound waves into the effective medium (M), by means of its ultrasound-emitting surface (Pz-o) and through the thin wall (W) and its ultrasound-emitting surface (Wo), wherein the thin wall (W) is firmly connected with or coalesced with the encapsulation (K), on the circumference side, in terms of material, wherein all of the corners and edges present on the encapsulation are rounded off, wherein the thin wall and the encapsulation consist of a hard material having a low damping coefficient, in particular of a hard, amorphous plastic, wherein the wall thickness (D) of the thin wall is equal to/less than a millimeter, wherein the ultrasound-emitting side/surface (Pz-o) of the electromechanical transducer (Pz) and the thin wall (W) are inseparably and directly connected with or adhered to one another with a very thin layer of an adhesive having the low damping coefficient, wherein the ultrasound-conducting/ultrasound-emitting surface (Wo) of the thin wall (W), which surface faces away from the electromechanical transducer (Pz), assumes its position, in terms of height, in an individual case, within the bristle field/the sonic field/the medium (M), between the position (Wo), at which the side/plane of the basic element (Bt-o), which firmly carries the bristles (B), which side also faces the effective medium, also lies, and the position (Wm), which essentially corresponds to half the height of the bristles (B) being used, in each instance, wherein the basic element (Bt-o) that firmly carries the bristles is firmly connected, in terms of material, with the body (Bt) of the carrier of the interchangeable brush head, and/or not connected, wherein the thin wall (W), the encapsulation (K), and the body (Bt) of the carrier of the interchangeable brush head are connected, in terms of material, in any case, with the neck (H) that stands in the axial connection with the body (Bt) of the carrier of the interchangeable brush head, wherein the electromechanical transducer (Pz) emits the energy produced by the ultrasound waves or by the mechanical vibrations in an axial direction that is parallel or essentially parallel to the expanse direction of the bristles.

The vertical double arrows shown in FIG. 1 and the concentric "wave symbols" indicate the expanse direction of the ultrasound waves, as these are introduced into the effective medium (M) from the electromechanical transducer (Pz) and the conductive, thin wall (W), i.e. that the electromechanical transducer (Pz) emits the energy produced by the ultrasound waves or by the mechanical vibrations in an axial direction that is parallel or essentially parallel to the expanse direction of the bristles.

The reference symbol (Sch) (=sonic field) indicates the spatial region of action of the sonic field that occurs in the effective medium, which goes beyond the spatial volume of the bristle field.

This is the general form according to the invention.

It includes the two fundamental embodiments:

a.) that the entire body (Bt) of the carrier of the interchangeable brush head with the bristles (B) firmly affixed on it, with the firmly connected electromechanical transducer (Pz), the firmly connected thin wall (W), the firmly connected encapsulation (K), the firmly connected neck (H), and further elements, which will still be described, is interchangeable in its entirety, as a functioning product, as well as b.) that only the replacement insert (Bt-E) with the bristles (B) firmly situated on it is exchangeable, and is built separately, wherein the body (Bt) of the carrier of the interchangeable brush head, the neck (H), the electromechanical transducer (Pz), the thin wall (W), the encapsulation (K), together with further elements, which will still be described, are not exchangeable in normal, usual use, i.e. that in this fundamental embodiment, the entire body (Bt) of the carrier of the interchangeable brush head is firmly connected, mechanically and electrically, with the handle (Hg) of the entire ultrasound toothbrush (Uz), directly by means of the neck (H).

The newly developed, very high-performance materials or plastics, such as the plastic graphene, for example, which represents a modification of carbon with a two-dimensional structure, and which develops very great hardness and rigidity at extremely thin layers, with a simultaneously low damping coefficient for passing the ultrasound waves through are also suitable for use as the encapsulation (K), as the thin wall (W), as the basic element (Bt-o) that firmly carries the bristles (B), as the neck (H), as the body of the replacement insert (Bt-E), and also as the entire body (Bt) of the carrier of the interchangeable brush head.

In the future, further progress can be expected in this technical field.

The following plastics are already available as hard, amorphous plastics having a low damping coefficient for conducting/passing along ultrasound waves, for example the following plastics: polycarbonate (PC), polystyrene (PS), polymethylmethacrylate (PMMA), acrylonitrile butadiene styrene (ABS), etc., for use as the encapsulation (K), as the thin wall (W), as the basic element (Bt-o) that firmly carries the bristles (B), as the body of the replacement insert (Bt-E), as the neck (H), and also as the entire body (Bt) of the carrier of the interchangeable brush head.

In the future, further progress can be expected in this technical field, as well.

Many materials are fundamentally suitable as a material for the electromechanical transducer (Pz), above all PZT ceramics (lead-zirconate-titanate), in particular the PZT ceramics of the material groups 5 and 8, specifically because of their mechanical, electrical, physical, and production-technology properties.

The interchangeable brush head according to the invention, with ultrasound action for ultrasound devices, acts together in connection with a toothpaste having the lowest possible damping coefficient.

Figure 2:
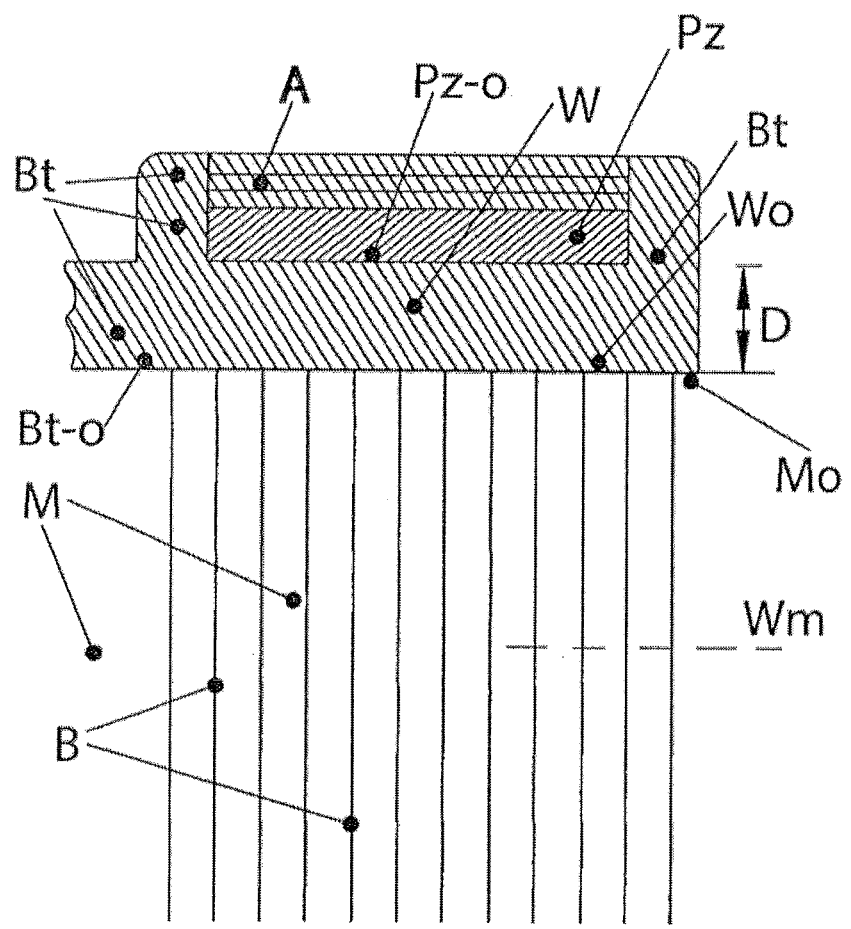
FIG. 2, in a frontal and/or side view, schematically shows the interchangeable brush head with ultrasound action, in the fundamental embodiment a.)

FIG. 2, in a frontal and/or side view, schematically shows the interchangeable brush head with ultrasound action for ultrasound devices, in particular for an ultrasound toothbrush and/or for an ultrasound therapy and massage device, specifically in the fundamental embodiment a.), wherein the thin wall (W) and the encapsulation (K) are connected, in terms of material, with the basic element (Bt-o) that firmly carries the bristles (B), and the body (Bt) of the carrier of the interchangeable brush head.

Furthermore, FIG. 2 schematically shows that the thin wall (W), the encapsulation (K), the basic element (Bt-o), and the body (Bt) of the carrier of the interchangeable brush head belong together as a body, that they, together with the neck (H) situated in the axially uninterrupted connection with the body (Bt) of the carrier of the interchangeable brush head, form a one-part piece before application of the bristles, wherein this one-part piece consists of a hard material having the low damping coefficient, in particular of a hard, amorphous plastic, wherein a covering (A) is situated above the rear side of the electromechanical transducer (Pz), closing any gaps/closing the contour, and closing any channels, as well as protecting the electromechanical transducer (Pz) mechanically, electrically, and chemically.

Figure 3:
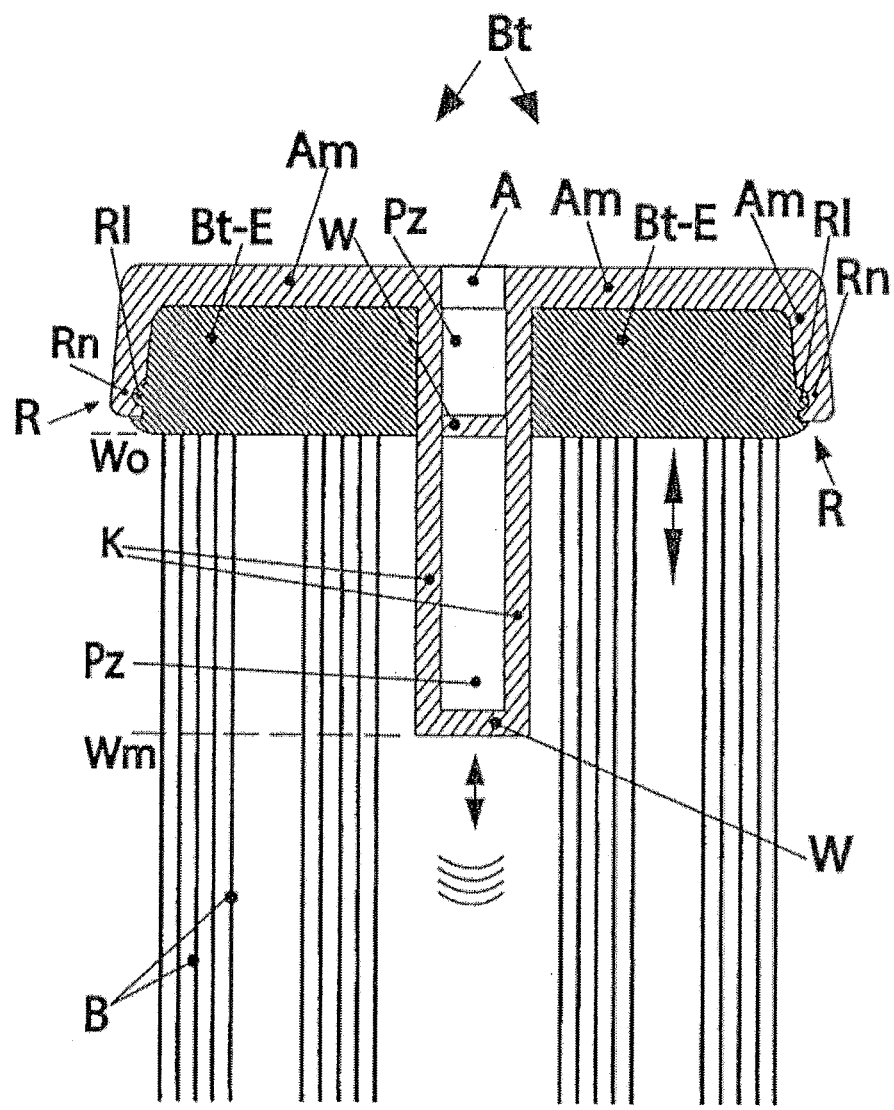
FIG. 3, in a frontal view, schematically shows the interchangeable brush head with ultrasound action, in the fundamental embodiment b.)

FIG. 3, in a frontal view, schematically shows the interchangeable brush head with ultrasound action, specifically in the fundamental embodiment b.), wherein it can be seen that the thin wall (W), the encapsulation (K), which firmly encloses the electromechanical transducer (Pz), in terms of its height expanse, in completely seamless manner and, in terms of material, from all four sides, and which carries the thin wall and forms a closure, in terms of height, and the accommodation recess (Am) that is firmly connected with the encapsulation, in terms of material, are firmly connected, in terms of material, with the neck (H) that is situated in the uninterrupted axial extension of the accommodation recess, and are firmly connected with one another, in terms of material, as a whole, and that they are produced in one part, in terms of production technology, before the bristles are applied, wherein the end of the neck (H) that axially faces away from the accommodation recess (Am) is firmly and inseparably connected with the handle (Hg) of the ultrasound toothbrush (Uz), mechanically and electrically, wherein all the corners and edges of the encapsulation (K) are rounded off, and wherein a covering (A) is situated above the rear side of the electromechanical transducer (Pz), closing any gaps/closing the contour, and closing any channels, and also that the covering covers the electromechanical transducer (Pz) and the supply cables (L) situated in the cable channel (Kk), which are laid from a certain region along the elongated rear side of the neck (H) all the way to the solder points on the piezoelectric element, protecting them mechanically, electrically, and chemically.

Furthermore, FIG. 3 schematically shows that the body (Bt) of the carrier of the interchangeable brush head consists of a bottom and of the walls that completely enclose the bottom on the circumference, essentially vertically, that the accommodation recess (Am) that is open on one side is built from this, wherein the outer design form of the replacement insert (Bt-E) that firmly carries the bristles (B), which insert is produced separately, is adapted to the inner contours of the accommodation recess (Am) that is open on one side, for reciprocal engagement.

Furthermore, FIG. 3 also schematically shows that a stable but releasable engagement connection (R) is formed between the replacement insert (Bt-E) that carries the bristles and the body (Bt) of the carrier of the interchangeable brush head, i.e. the accommodation recess (Am), in that the engagement grooves (Rn), multiple ones of which are affixed on the circumference side, on the inner sides of the entire wall, in the region of the accommodation recess (Am) that is close to the opening, stand in engagement with the engagement strips (Rl) of the replacement insert (Bt-E), multiple ones of which are also present, also affixed on the circumference side and corresponding with them, i.e. that the engagement strips (Rl) engage into the engagement grooves (Rn), wherein engagement and unlocking take place in a direction that is parallel or essentially parallel to the longitudinal expanse of the bristles.

FIG. 3, with the reference symbol (Wo), shows the lowest position, in terms of height, of the ultrasound-emitting surface of the thin wall (W), where it is shown that the position (Wo) is situated in the same plane as the side (Bt-o) of the basic element that faces the effective medium, and this brings with it the most advantages in terms of safety technology, applications, and production technology.

The same FIG. 3 also, with the reference symbol (Wm) and the horizontal, interrupted line, shows the highest position, in terms of height, of the ultrasound-emitting surface of the thin wall (W) in relation to the height of the bristles (B) used, wherein this height (position) essentially corresponds to half the height of the bristles (B) being used, in each instance.

The height or the position of the ultrasound-emitting surface of the thin wall (W) must, of course, always pay attention to the safety and the ease of operation by the user and the requirements in terms of design/production technology, and thereby stands in collision with the desire of wanting to achieve an even more intensive sonic power and sonic intensity in this way, of wanting to achieve a conceivably short path of the ultrasound-emitting surface to the teeth.

This exemplary embodiment shows an electromechanical transducer (Pz) affixed axially in the center of the body (Bt) of the carrier of the interchangeable brush head, wherein the object of the invention is not, of course, restricted to this exemplary embodiment only.

Figure 4:
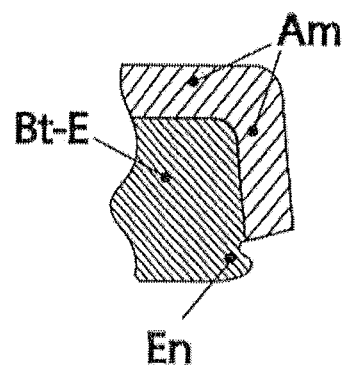
FIG. 4 schematically shows a cross-section through the wall of the accommodation recess.

FIG. 4 schematically shows, in a cross-section through the wall of the accommodation recess (Am), that a small-area unlocking groove (En) is built in at the height of the opening region of the accommodation recess (Am), on the outside of the interchangeable replacement insert (Bt-E), in particular in the immediate vicinity of the neck (H), wherein a matching incision is provided at the spatially corresponding location of the side wall of the accommodation recess, that in this way, unlocking can be undertaken by means of a lever effect, using the tip of a tool, wherein all the corners and edges are rounded off in the unlocking region, wherein engagement and unlocking take place in a direction that is parallel or essentially parallel to the longitudinal expanse of the bristles.

Figure 5:
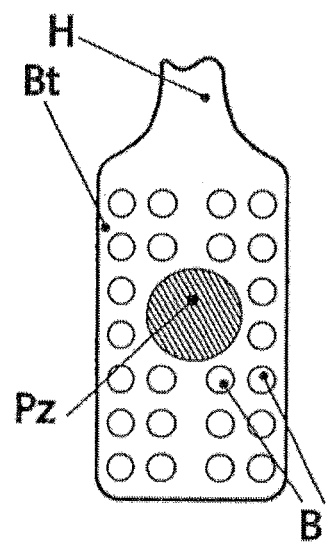
FIG. 5, in a top view, schematically shows the body, according to the invention, of the carrier of the interchangeable brush head, and a round electromechanical transducer placed approximately in the geometrical center.

FIG. 5, in a top view, schematically shows the body (Bt), according to the invention, of the carrier of the interchangeable brush head, and a round electromechanical transducer (Pz) placed approximately in the geometrical center.

Figure 6:
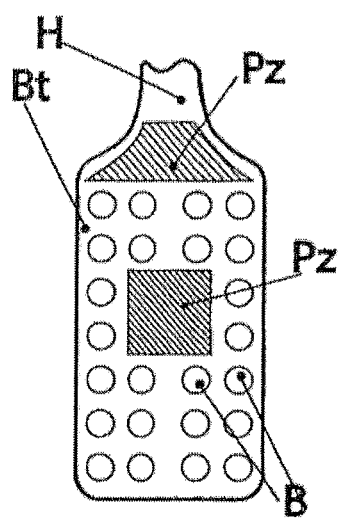
FIG. 6, in a top view, schematically shows the body, according to the invention, of the carrier of the interchangeable brush head, and a square, quadrangular electromechanical transducer placed approximately in the geometrical center, wherein a second electromechanical transducer in an essentially trapezoid shape is furthermore affixed in the axial connecting region between the bristle field and the neck.

FIG. 6, in a top view, schematically shows the body (Bt), according to the invention, of the carrier of the interchangeable brush head, and a square, quadrangular electromechanical transducer (Pz) placed approximately in the geometrical center, wherein a second electromechanical transducer (Pz) in an essentially trapezoid shape is furthermore affixed in the axial connecting region between the bristle field and the neck (H), wherein the base side of the trapezoid faces the bristle field.

Figure 7:
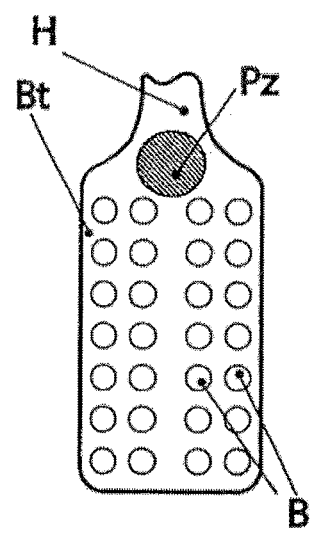
FIG. 7, in a top view, schematically shows the body, according to the invention, of the carrier of the interchangeable brush head, and a round electromechanical transducer affixed on the inside, specifically in an axial connecting region between the bristle field and the neck.

FIG. 7, in a top view, schematically shows the body (Bt), according to the invention, of the carrier of the interchangeable brush head, and a round electromechanical transducer (Pz) affixed on the inside, specifically in an axial connecting region between the bristle field and the neck (H).

Figure 8:
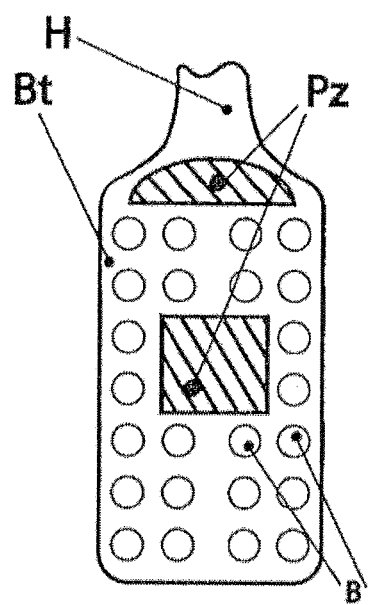
FIG. 8, in a top view, schematically shows the body, according to the invention, of the carrier of the interchangeable brush head, and a square, quadrangular electromechanical transducer placed approximately in the geometrical center, wherein a second electromechanical transducer in a shape approximately that of a circle segment is furthermore affixed in the axial connecting region between the bristle field and the neck.

FIG. 8, in a top view, schematically shows the body (BT), according to the invention, of the carrier of the interchangeable brush head, and a square, quadrangular electromechanical transducer (Pz) placed approximately in the geometrical center, wherein a second electromechanical transducer (Pz) in a shape approximately that of a circle segment is furthermore affixed in the axial connecting region between the bristle field and the neck (H), wherein the base side of the shape in the manner of a circle segment faces the bristle field.

Figure 9:
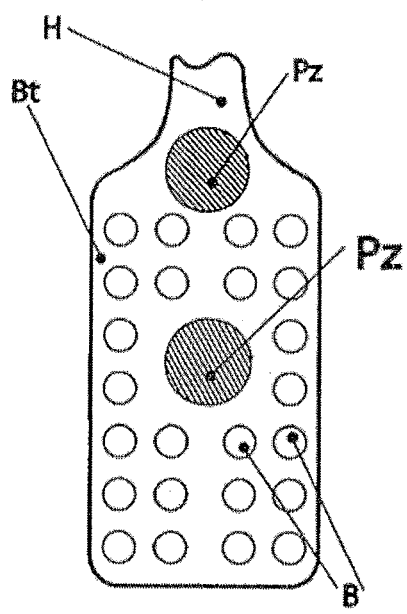
FIG. 9, in a top view, schematically shows the body, according to the invention, of the carrier of the interchangeable brush head and the two round electromechanical transducers.

FIG. 9, in a top view, schematically shows the body (Bt), according to the invention, of the carrier of the interchangeable brush head and the two round electromechanical transducers (Pz), wherein the one electromechanical transducer is placed approximately in the geometric center, and wherein the other electromechanical transducer is placed in the axial connecting region between the brush field and the neck (H).

Figure 10:
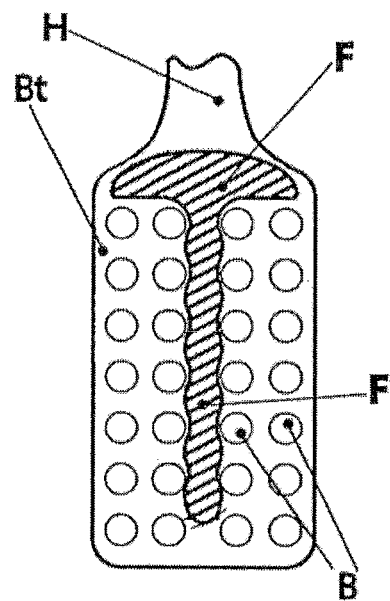
FIG. 10, in a top view, schematically shows the body, according to the invention, of the carrier of the interchangeable brush head, where it is shown that on the side of the basic element that firmly carries the bristles, which side faces the bristles, a thin piezoelectric film is applied.

FIG. 10, in a top view, schematically shows the body (Bt), according to the invention, of the carrier of the interchangeable brush head, where it is shown that on the side of the basic element (Bt-o) that firmly carries the bristles, which side faces the bristles, at least one thin, piezoelectric element, in particular a thin piezoelectric film (F), is applied, wherein the thin piezoelectric element and/or the thin piezoelectric film (F) emits the ultrasound waves in an axial direction that is parallel or essentially parallel to the expanse direction of the bristles.

The "screw shape" shown, with a planar, approximately semicircular-type "head part" in the connecting region between the bristle field and the part of the neck situated in an axial extension can already be used today, specifically by means of what are called patch transducers or film transducers, for example from the German company Pi Ceramic GmbH, which are already available as piezoelectric/piezoceramic actuators.

The newly developed, very high-performance materials or plastics, such as the plastic graphene, for example, which represents a modification of carbon with a two-dimensional structure, and which develops very great hardness and rigidity at extremely thin layers, with a simultaneously low damping coefficient for passing the ultrasound waves through are also suitable for use as the encapsulation (K) with the thin piezoelectric film (F) or with the thin applied layer of the piezoelectric material.

In the future, further progress can be expected in this technical field.

Figure 11:
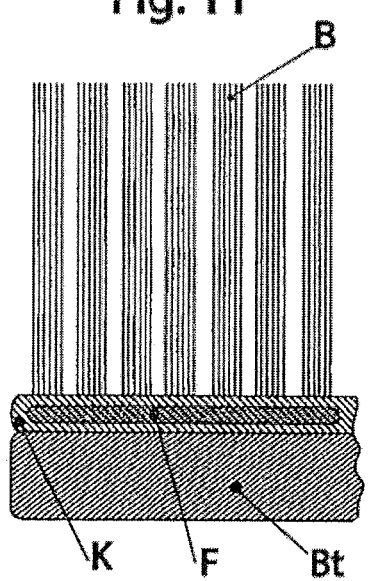
FIG. 11 schematically shows the thin piezoelectric film sheathed from all sides by a thin encapsulation, i.e. is firmly mechanically encapsulated in the same encapsulation.

FIG. 11 schematically shows that the thin piezoelectric element—in particular a thin piezoelectric film (F) on the side of the basic element (Bt-o) that firmly carries the bristles, which side faces the bristles, is sheathed from all sides by a thin encapsulation (K), i.e. is firmly mechanically encapsulated in the same encapsulation, wherein the thin encapsulation (K) consists of a hard material with the low damping coefficient, in particular of a hard, amorphous plastic, and wherein the thin piezoelectric film (F) and/or the thin piezoelectric element and the inner wall of the encapsulation. (K) are firmly and directly connected with or adhered to one another with a hard to rigid adhesive with the low damping coefficient, and wherein the surface of the encapsulation that faces away from the free bristle ends is directly connected with or adhered to the body (Bt) of the carrier of the interchangeable brush head.

Figure 12:
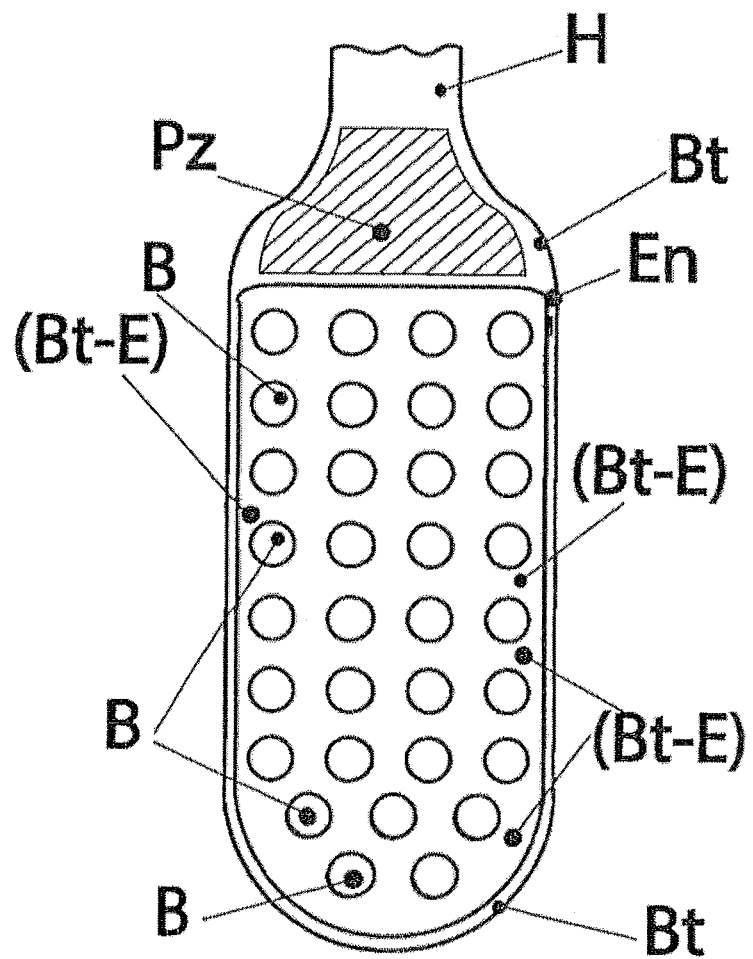
FIG. 12 schematically shows the interchangeable replacement insert with ultrasound effect, according to the invention, in a top view, where it is evident that the electromagnetic transducer is placed in the immediate axial connecting region between the accommodation recess, i.e. the bristle field, and the axially connecting region of the neck in the body of the carrier of the interchangeable brush head.

FIG. 12 schematically shows the interchangeable replacement insert (Bt-E) with ultrasound effect, according to the invention, in a top view, where it is evident that the electromagnetic transducer (Pz) is placed in the immediate axial connecting region between the accommodation recess (Am), i.e. the bristle field, and the axially connecting region of the neck (H) in the body (Bt) of the carrier of the interchangeable brush head, wherein the electromechanical transducer (Pz) has an essentially trapezoid shape in a top view, wherein the longer base side of this trapezoid faces the bristle field, i.e. that the shape of the electromechanical transducer (Pz), in a top view, maximally adapts itself to the outer contours of the body (Bt) of the carrier of the interchangeable brush head in that region, symmetrically spreading out over the area.

Figure 13:
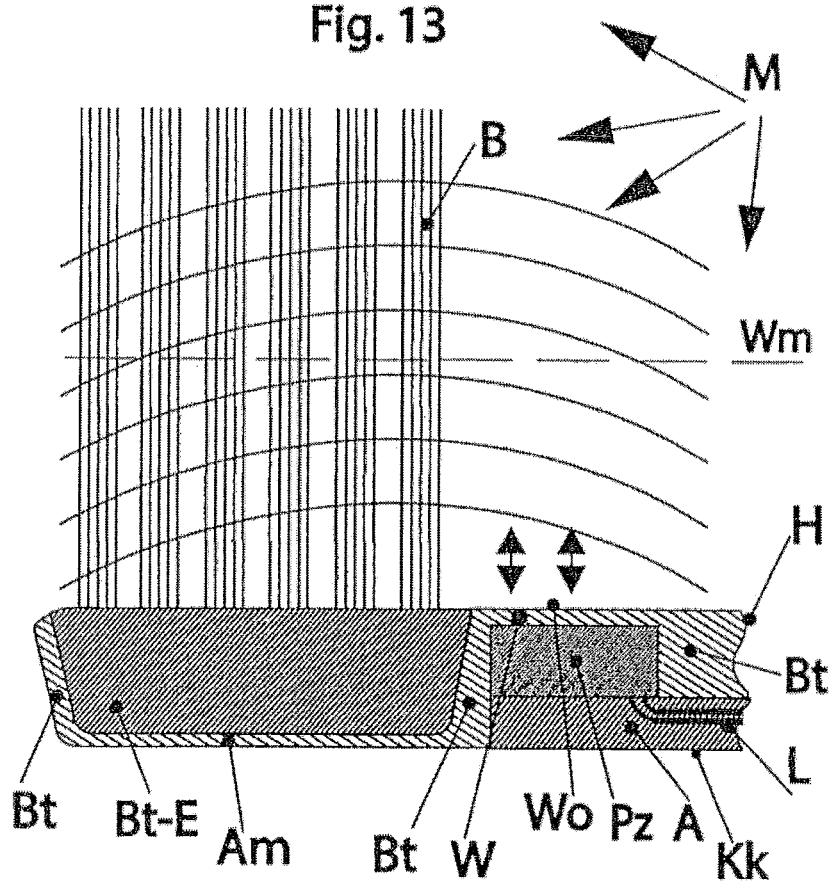
FIG. 13 schematically shows the interchangeable replacement insert with ultrasound action, according to the invention, in a side view, where it is shown that the electromechanical transducer is placed in the immediate axial connecting region between the accommodation recess, i.e. the bristle field, and the axially connecting region of the neck in the body of the carrier of the interchangeable brush head.

FIG. 13 schematically shows the interchangeable replacement insert (Bt-E) with ultrasound action, according to the invention, in a side view, where it is shown that the electromechanical transducer (Pz) is placed in the immediate axial connecting region between the accommodation recess (Am), i.e. the bristle field, and the axially connecting region of the neck (H) in the body (Bt) of the carrier of the interchangeable brush head. The figure also shows the progression of the cable channel (Kk) and of the supply cables (L) that are laid in it. It also shows the body of the interchangeable replacement insert (Bt-E) engaged into the accommodation recess (Am), and the bristles (B) attached to it, as well as the highest position, in terms of height, in an individual case, of the ultrasound-emitting surface of the thin wall (W) in relation to the height of the bristles (B) used, with the reference symbol (Wm).

The vertical double arrows that are present and the concentric "wave symbols" show the expanse direction of the ultrasound waves emitted by the piezoelectric transducer (Pz) through the thin wall (W), which waves run parallel or essentially parallel to the bristles (B).

The reference symbol (M) with the arrows that point in different directions stands for the spatially effective medium, which consists of a mixture of water, saliva, and toothpaste.

Figure 14:
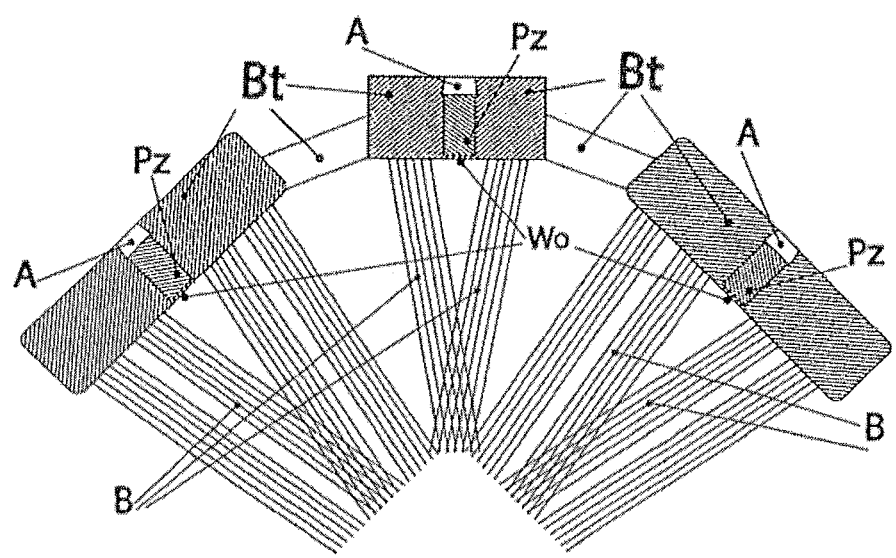
FIG. 14 schematically shows the interchangeable brush head (triple head) according to the invention, from which it is evident that the entire interchangeable body of the carrier of the interchangeable brush head consists of three brush head segments that are offset radially from one another, in each instance, and physically connected with one another.

FIG. 14 schematically shows the interchangeable brush head (triple head) according to the invention, from which it is evident that the entire interchangeable body (Bt) of the carrier of the interchangeable brush head consists of three brush head segments that are offset radially from one another, in each instance, and physically connected with one another, wherein the entire body of the triple brush head (Bt), including the neck (H), the thin wall (W), the connection elements, and the encapsulation (K), is built in one piece, at first without bristles, specifically from a hard, amorphous plastic that has a low damping coefficient, and wherein at least one brush head segment and/or its immediate vicinity has the electromechanical transducer (Pz).

Such a special exemplary embodiment offers the advantage that a tooth area is cleaned from all three sides simultaneously, which makes tooth cleaning about three times faster, and also means that such a brush head shape can bind the actively cleaning medium (M) significantly more in the entire region of the sonic field, which significantly increases the effectiveness of the power emitted by the ultrasound waves.

Figure 15:
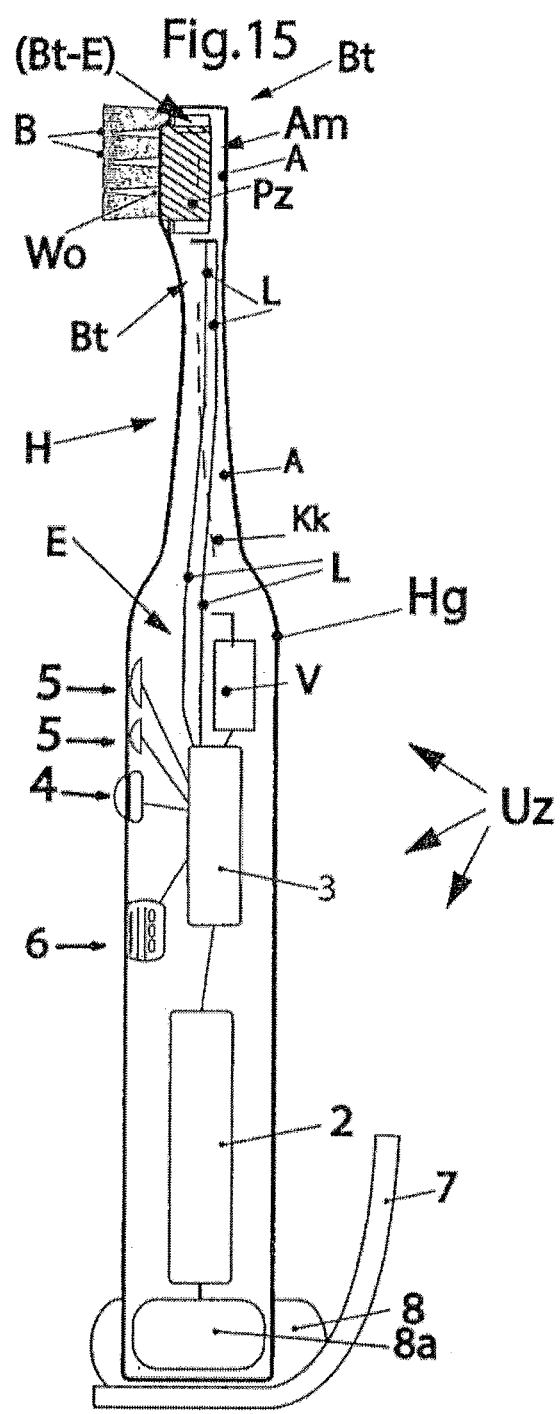
FIG. 15 schematically shows the interchangeable brush head according to the invention in the fundamental embodiment b.) in a side view, specifically together with the entire body of the ultrasound toothbrush, where it can be seen that the power supply of the rechargeable battery comes from an electrical/electronic induction apparatus situated in the handle.

FIG. 15 schematically shows the interchangeable brush head according to the invention in the fundamental embodiment b.) in a side view, specifically together with the entire body of the ultrasound toothbrush (Uz), where it can be seen that the power supply of the electric power supply unit, i.e. of the rechargeable battery (2), comes from an electrical/electronic induction apparatus (8, 8a) situated in the handle (Hg). The entire device and its components is/are supplied with electricity by the rechargeable battery. A control and electronics unit (3) generates the high-frequency currents that are then conducted to the electromechanical transducer (Pz) by the electronic end stage (E) by means of the supply cables (L), and where then, the ultrasound waves are generated and passed on by the electromechanical transducer (Pz).

There, it can also be seen that a covering (A) is situated above the rear side of the electromechanical transducer (Pz), wherein the covering covers the electromechanical transducer (Pz) and the supply cables (L) situated in the cable channel (Kk), which are laid from a specific region along the elongated rear side of the neck (H) all the way to the solder points on the piezoelectric element, protecting them mechanically, electrically, and chemically, and wherein the covering (A) continuously adapts to the cross-section progression of the body (Bt) of the carrier of the interchangeable brush head and of the neck (H), in terms of their respective longitudinal expanse. The progression of the cable channel (Kk) is indicated by the somewhat vertical broken line. Additional vibration operation is made possible by means of the vibrator (V).

FIG. 15 also schematically shows the region of the body (Bt) of the carrier of the interchangeable brush head, where the replacement insert (Bt-E) with the bristles (B) situated on it and engaged in the accommodation recess (Am) is shown.

For the sake of completeness, the function displays (5), the operating switch or programming knob (4), the display (6), and the holder of the charging station (7) present in the handle are also shown.

Figure 16:
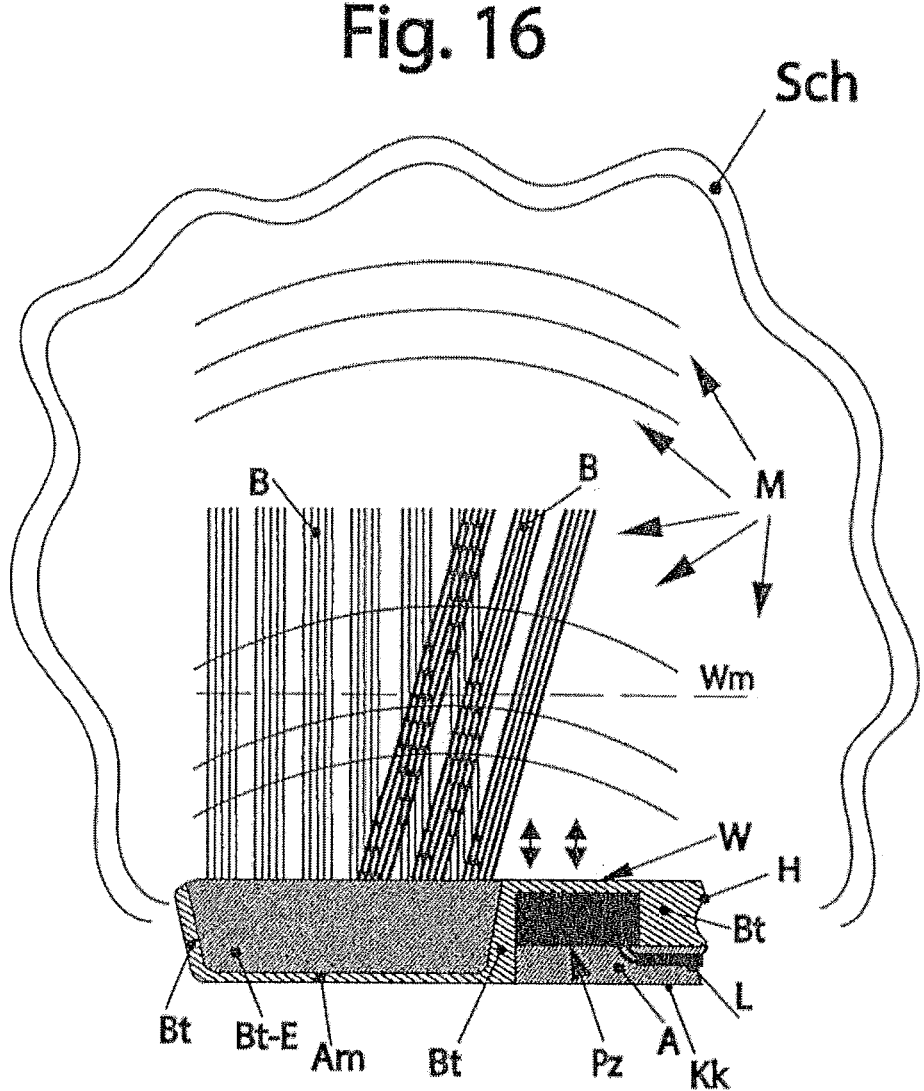
FIG. 16 schematically shows the interchangeable brush head with ultrasound action, according to the invention, in a side view, where it is shown that the electromechanical transducer is placed in the immediate axial connecting region between the accommodation recess or the bristle field and the axially connecting region of the neck in the body of the carrier of the interchangeable brush head.

FIG. 16 schematically shows the interchangeable brush head with ultrasound action, according to the invention, in a side view, where it is shown that the electromechanical transducer (Pz) is placed in the immediate axial connecting region between the accommodation recess (Am) or the bristle field and the axially connecting region of the neck (H) in the body (Bt) of the carrier of the interchangeable brush head, where furthermore, it is also shown that at least some bristle bundles on the end region of the bristle field that axially faces the neck (H) are inclined toward the same region of the neck. This is shown by the bristles (B) that are drawn with bold lines.

This has the advantage that in this way, even more volume/mass of liquids from the effective medium (M), consisting of water, saliva, and toothpaste, are bound in the bristle field and in the further-reaching sonic field, so that in this way, the efficiency of the transfer of energy by the ultrasound waves is even further increased.

FIG. 16 also shows the progression of the cable channel (Kk) and of the supply cables (L) laid in it. It also shows the body of the replacement insert (Bt-E) engaged in the accommodation recess (Am) and the bristles (B) attached on it, as well as the highest position, in terms of height, of the ultrasound-emitting surface of the thin wall (W) in relation to the height of the bristles (B) used, by means of the reference symbol (Wm).

The vertical double arrows that are present and the concentric "wave symbols" show the expanse direction of the ultrasound waves emitted by the piezoelectric transducer (Pz) through the thin wall (W), which waves run parallel or essentially parallel to the bristles (B) that are used.

The reference symbol (M) with the arrows that point in different directions stands for the spatially effective medium, which consists of a mixture of water, saliva, and toothpaste, and the reference symbol (Sch) stands for the even farther-reaching spatial region of the sonic field (Sch), in comparison with the bristle field.

Figure 17:
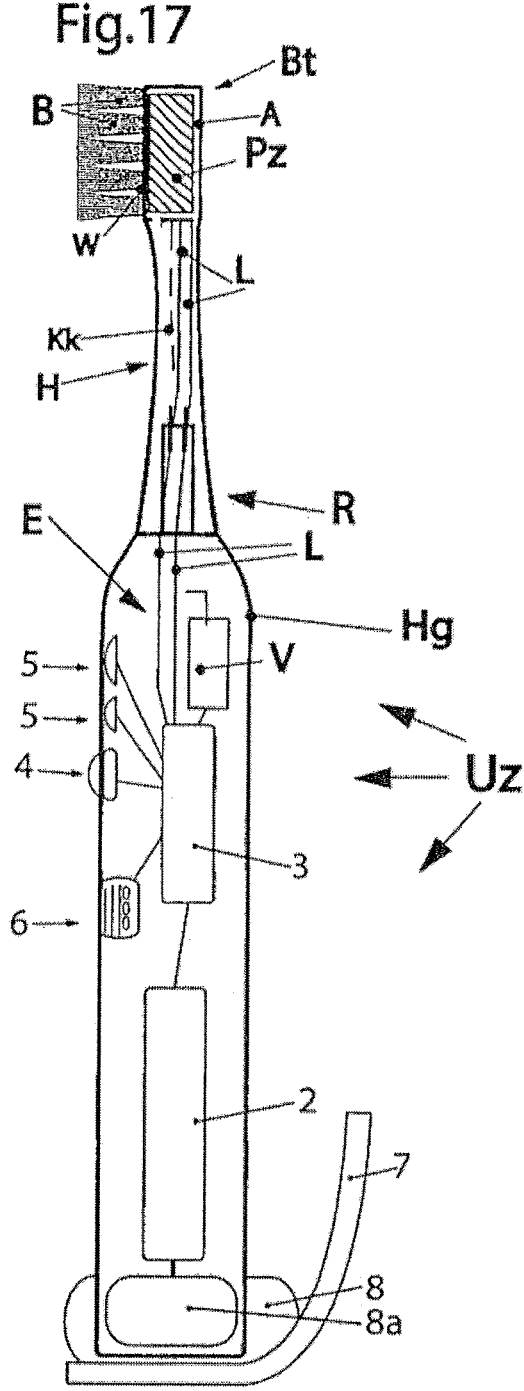
FIG. 17 schematically shows the interchangeable brush head according to the invention in the fundamental embodiment a.), in a side view, together with the entire body of the ultrasound toothbrush, where the end region of the neck axially facing away from the bristle field has an electrical and mechanical engagement connection.

FIG. 17 schematically shows the interchangeable brush head according to the invention in the fundamental embodiment a.), in a side view, specifically together with the entire body of the ultrasound toothbrush (Uz), where it can be seen that the end region of the neck (H), which region axially faces away from the bristle field, has an electrical and mechanical engagement connection (R), where the torque-proof mechanical engagement connection (R) comes about by means of a journal of the handle (Hg) of the ultrasound toothbrush (Uz), which journal is polygonal in cross-section, and the corresponding gap in the lower region of the neck (H), wherein at the same time, the electrical connection with the completely interchangeable brush head is produced by means of the metal pins that project out of the same journal and the matching connecting sleeves in the counterpart of the neck (H).

FIG. 17 also shows the region of the body (Bt) of the carrier of the interchangeable brush head, where it can be seen that the electromechanical transducer (Pz) is firmly affixed in the body (Bt) of the carrier of the interchangeable brush head, and thereby cannot be replaceable, i.e. that such a brush head must be replaced in its entirety, something that is not particularly environmentally friendly and does not save costs.

For the remainder, the same information provided with regard to the exemplary embodiment in FIG. 15 applies to this exemplary embodiment.

Figure 18:
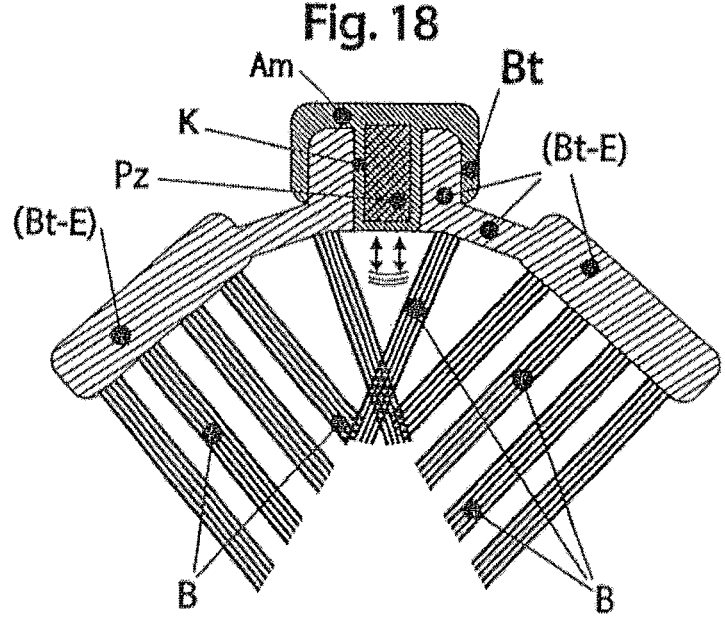
FIG. 18 schematically shows that the interchangeable (triple head) replacement insert consists of the one basic replacement insert placed radially centered, and of the three brush head segments on it, each offset radially relative to one another and physically connected with one another.

FIG. 18 schematically shows that the interchangeable (triple head) replacement insert (Bt-E) consists of the one basic replacement insert (Bt-E) placed radially centered, and of the three brush head segments on it, each offset radially relative to one another and physically connected with one another, wherein the body (Bt) of the carrier of the interchangeable brush head, which carrier is not interchangeable here—including the accommodation recess (Am), the neck (H), the thin wall (W), and the encapsulation (K)—is built in one piece, specifically from a hard, amorphous plastic, which has a low damping coefficient, wherein the electromechanical transducer (Pz) is situated on the inside, in the encapsulation (K) that is situated radially centered or in the immediate vicinity, wherein each brush head segment has its own bristle field, wherein the replacement insert (Bt-E) comprises all three brush head segments in one piece, i.e. wherein the replacement insert (Bt-E) is produced in one piece, at first without bristles.

Such a particular exemplary embodiment offers the advantage that a tooth area is cleaned from all three sides simultaneously, which makes tooth cleaning about three times faster, and also that such a brush head shape can bind the actively cleaning medium (M) significantly more in the entire region of the sonic field, which significantly increases the effectiveness of the power emitted by the ultrasound waves. The exemplary embodiment also shows that the bristles (B) situated in the center segment reciprocally intersect with their respective bristle ends.

Figure 19:
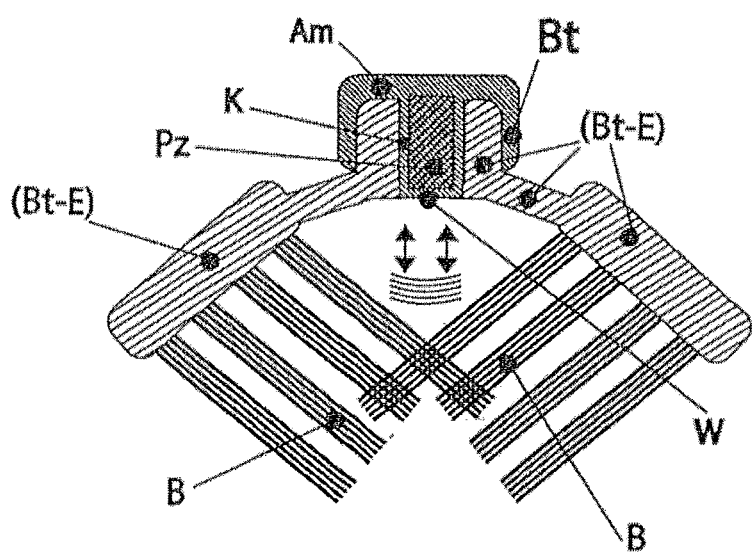
FIG. 19 schematically shows that the interchangeable double head replacement insert consists of the one basic replacement insert that is placed radially centered and does not have its own bristle field, and the two—one on the left side of the basic replacement insert, one on the right side of the basic replacement insert—brush head segments on it, offset radially from one another and physically connected with one another.

FIG. 19 schematically shows that the interchangeable double head replacement insert (Bt-E) consists of the one basic replacement insert (Bt-E) that is placed radially centered and does not have its own bristle field, and the two—one on the left side of the basic replacement insert, one on the right side of the basic replacement insert—brush head segments on it, offset radially from one another and physically connected with one another, wherein the body (Bt) of the carrier of the interchangeable brush head, which carrier is not interchangeable here—including the accommodation recess (Am), the neck (H), the thin wall (W), and the encapsulation (K)—is built in one piece, specifically from a hard, amorphous plastic, which has a low damping coefficient, wherein each of the two brush head segments has its own bristle field, wherein in the engaged state, the electromechanical transducer (Pz), which is firmly housed in the encapsulation (K) of the body (Bt) of the carrier of the interchangeable brush head, which carrier is not interchangeable here, passes the energy of the ultrasound waves, in terms of its function, directly into the effective medium, and passes it through into the effective medium in the bristle field region/in the sonic field region, out of the radially-geometrically center region of the immediate basic replacement insert (Bt-E), i.e. out of the region of its central opening, through the thin wall (W), wherein at least some bristle bundles intersect one another in the frontal view of the replacement insert (Bt-E), in the region of the free bristle ends.

The inner elongated rows of bristle bundles, in each instance, are provided with longer bristles in this exemplary embodiment, so that the intersecting region of the bristles comes about even more clearly. In this way, this elastic intersecting region replaces the eliminated third head, in terms of its function, but does bring with it design facilitation and simpler production.

Figure 20:
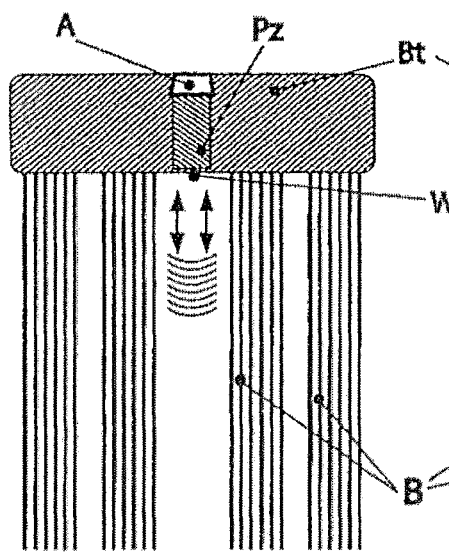
FIG. 20, in a frontal view, schematically shows the body of the carrier of the interchangeable brush head, with an electromechanical transducer placed axially centered between the elongated bristle bundle rows, with the bristles that are set upright essentially perpendicular to the side of the basic element that firmly carries the bristles, which side faces the effective medium.

FIG. 20, in a frontal view, schematically shows the body (Bt) of the carrier of the interchangeable brush head, with an electromechanical transducer (Pz) placed axially centered between the elongated bristle bundle rows, with the bristles (B) that are set upright essentially perpendicular to the side of the basic element (Bt-o) that firmly carries the bristles (B), which side faces the effective medium (M).

Figure 21:
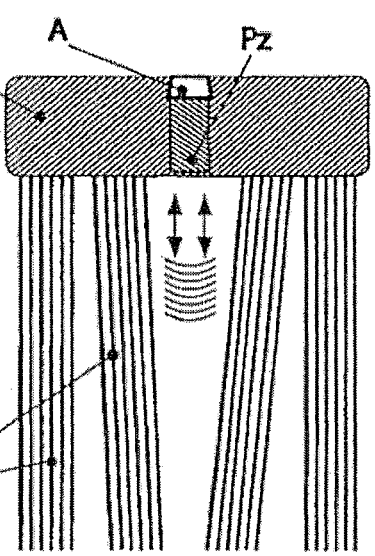
FIG. 21, in a frontal view, schematically shows the body of the carrier of the interchangeable brush head, with an electromechanical transducer placed axially centered between the elongated bristle bundle rows, where an inner longitudinal row of the bristle bundles, in each instance, on the left side of the bristle field, is inclined toward the corresponding inner longitudinal row of the bristle bundles on the right side of the bristle field.

FIG. 21, in a frontal view, schematically shows the body (Bt) of the carrier of the interchangeable brush head, with an electromechanical transducer (Pz) placed axially centered between the elongated bristle bundle rows, where it can be seen that an inner longitudinal row of the bristle bundles, in each instance, on the left side of the bristle field, is inclined toward the corresponding inner longitudinal row of the bristle bundles on the right side of the bristle field. In this way, the sonic field and the bristle field are structured more uniformly.

Figure 22:
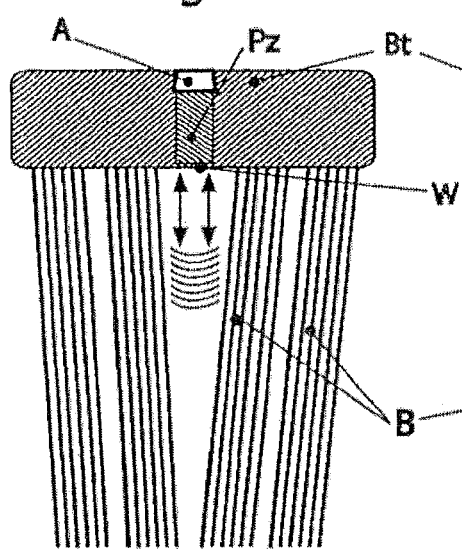
FIG. 22, in a frontal view, schematically shows the body of the carrier of the interchangeable brush head, with an electromechanical transducer placed axially centered between the elongated bristle bundle rows, where all the longitudinal rows on the left side of the bristle field, in each instance, are inclined toward all the corresponding longitudinal rows of the bristle bundles on the right side of the bristle field.

FIG. 22, in a frontal view, schematically shows the body (Bt) of the carrier of the interchangeable brush head, with an electromechanical transducer (Pz) placed axially centered between the elongated bristle bundle rows, where it can be seen that all the longitudinal rows on the left side of the bristle field, in each instance, are inclined toward all the corresponding longitudinal rows of the bristle bundles on the right side of the bristle field. This embodiment brings with it bundling of the bristle field and of the sonic field.

Figure 23:
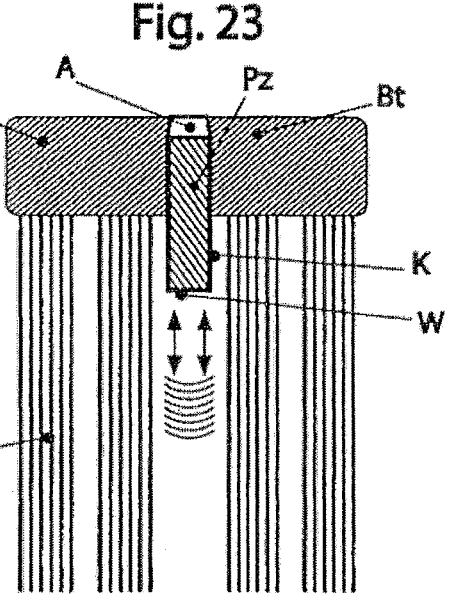
FIG. 23, in a frontal view, schematically shows the body of the carrier of the interchangeable brush head, with an electromechanical transducer placed axially centered between the elongated bristle bundle rows, with the bristles set upright essentially perpendicular to the side of the basic element that firmly carries the bristles, which side faces the effective medium.

FIG. 23, in a frontal view, schematically shows the body (Bt) of the carrier of the interchangeable brush head, with an electromechanical transducer (Pz) placed axially centered between the elongated bristle bundle rows, with the bristles (B) set upright essentially perpendicular to the side of the basic element (Bt-o) that firmly carries the bristles (B), which side faces the effective medium (M), wherein the sound-emitting side of the thin wall (W) reaches about 25% of the height of the bristles used, in terms of height.

Figures 24, 25:
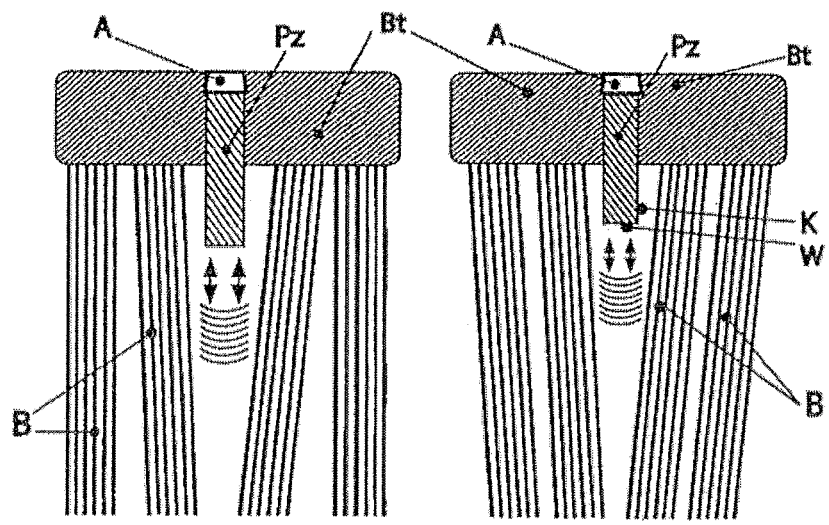
FIG. 24, in a frontal view, schematically shows the body of the carrier of the interchangeable brush head, with an electromechanical transducer placed axially centered between the elongated bristle bundle rows, where an inner longitudinal row of the bristle bundles on the left side of the bristle field, in each instance, is inclined toward the corresponding inner longitudinal row of the bristle bundles on the right side of the bristle field.
FIG. 25, in a frontal view, schematically shows the body of the carrier of the interchangeable brush head, with an electromechanical transducer placed axially centered between the elongated bristle bundle rows, where all the longitudinal rows on the left side of the bristle field, in each instance, are inclined toward all the corresponding longitudinal rows of the bristle bundles on the right side of the bristle field.

FIG. 24, in a frontal view, schematically shows the body (Bt) of the carrier of the interchangeable brush head, with an electromechanical transducer (Pz) placed axially centered between the elongated bristle bundle rows, where it can be seen that an inner longitudinal row of the bristle bundles on the left side of the bristle field, in each instance, is inclined toward the corresponding inner longitudinal row of the bristle bundles on the right side of the bristle field. In this way, the sonic field and the bristle field are structured more uniformly, wherein the sound-emitting side of the thin wall (W) reaches about 30% of the height of the bristles used, in terms of height.

FIG. 25, in a frontal view, schematically shows the body (Bt) of the carrier of the interchangeable brush head, with an electromechanical transducer (Pz) placed axially centered between the elongated bristle bundle rows, where it can be seen that all the longitudinal rows on the left side of the bristle field, in each instance, are inclined toward all the corresponding longitudinal rows of the bristle bundles on the right side of the bristle field. This embodiment brings with it bundling of the bristle field and of the sonic field, wherein the sound-emitting side of the thin wall (W) reaches about 20% of the height of the bristles used, in terms of height.

Figure 26:
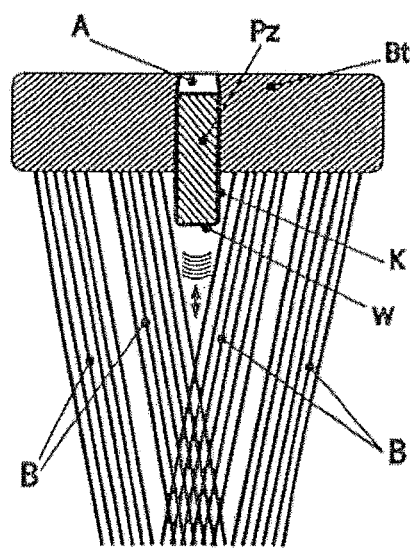
FIG. 26, in a frontal view, schematically shows the body of the carrier of the interchangeable brush head, with an electromechanical transducer placed axially centered between the elongated bristle bundle rows, where the inner bristle bundle rows that extend axially-longitudinally on the left side of the bristle field or of the replacement insert, in each instance, intersect with the corresponding inner longitudinal rows of the bristle bundles on the right side of the bristle field, in each instance.

FIG. 26, in a frontal view, schematically shows the body (Bt) of the carrier of the interchangeable brush head, with an electromechanical transducer (Pz) placed axially centered between the elongated bristle bundle rows, where it can be seen that the inner bristle bundle rows that extend axially-longitudinally on the left side of the bristle field or of the replacement insert (Bt-E), in each instance, intersect with the corresponding inner longitudinal rows of the bristle bundles on the right side of the bristle field, in each instance, wherein the sound-emitting side of the thin wall (W) reaches about 20% of the height of the bristles used, in terms of height. This brings with it the advantage that the emitted sonic power and the sonic intensity can be further increased, wherein the user is protected against injuries and breakdowns at the same time, since the electromechanical transducer (Pz) is well shielded by the intersecting bristle bundles in this regard.

Figure 27:
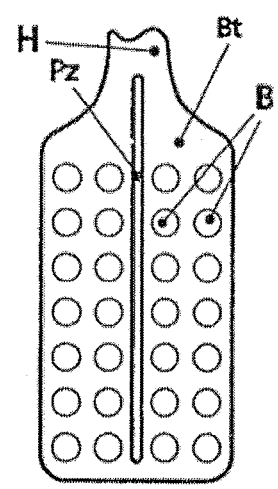
FIG. 27, in a top view, schematically shows the body of the carrier of the interchangeable brush head, with the bristles set up on it and an electromechanical transducer placed axially centered between the elongated bristle bundle rows.

FIG. 27, in a top view, schematically shows the body (Bt) of the carrier of the interchangeable brush head, with the bristles (B) set up on it and an electromechanical transducer (Pz) placed axially centered between the elongated bristle bundle rows.

Figure 28:
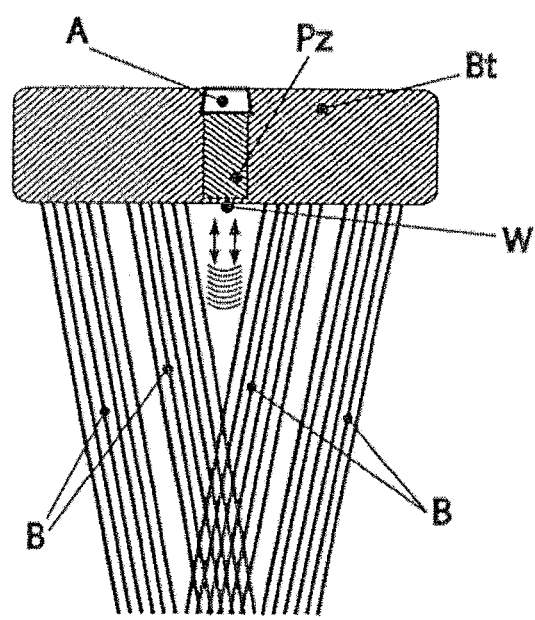
FIG. 28, in a frontal view, schematically shows the body of the carrier of the interchangeable brush head, with an electromechanical transducer placed axially centered between the elongated bristle bundle rows, where the inner bristle bundle rows that extend axially-longitudinally on the left side of the bristle field or of the replacement insert, in each instance, intersect with the corresponding inner longitudinal rows of the bristle bundles on the right side of the bristle field, in each instance.

FIG. 28, in a frontal view, schematically shows the body (Bt) of the carrier of the interchangeable brush head, with an electromechanical transducer (Pz) placed axially centered between the elongated bristle bundle rows, where it can be seen that the inner bristle bundle rows that extend axially-longitudinally on the left side of the bristle field or of the replacement insert (Bt-E), in each instance, intersect with the corresponding inner longitudinal rows of the bristle bundles on the right side of the bristle field, in each instance, wherein the sound-emitting side of the thin wall (W) reaches the lowest position (Wo), in terms of height.

This brings with it the advantage that the user is protected against injuries and breakdowns, since the electromechanical transducer (Pz) is well shielded by the intersecting bristle bundles in this regard.

An exemplary embodiment that is not shown contains such a structure of the object of the invention that the layer situated between the rear side of the electromechanical transducer (Pz) and the covering (A) is suitable for a reflective effect of the ultrasound waves in its main direction. Such layers are built on the basin of plastic foams, for example, mixed with metal dust. Polyurethane foam, for example, mixed with tungsten dust, is suitable for this.

A further exemplary embodiment that is not shown contains such a structure of the object of the invention that one or more substances that have a low damping coefficient for passing the ultrasound waves through are added to the material of the bristles, at least in part. Glass beads and/or various carbon compounds, for example, are suitable for this, as are newly developed materials such as the plastic graphene, for example, which represents a modification of carbon with a two-dimensional structure.

REFERENCE SYMBOL LIST a.)=fundamental embodiment a.), wherein the entire brush head with the electromechanical transducer (Pz) and the neck (H) is interchangeable
b.)=fundamental embodiment b.), wherein only the interchangeable insert (Bt-E) with the bristles (B) situated on it is interchangeable
(A)=covering of the cable channel (Kk), of the supply cables (L), and of the electromechanical transducer (Pz)
(Am)=accommodation recess
(B)=bristles
(Bt)=body of the carrier of the interchangeable brush head
(Bt-o)=side of the basic element that firmly carries the bristles (B), which side faces the effective medium (M)
(Bt-E)=interchangeable replacement insert with the bristles (B) thereon
(D)=wall thickness of the thin wall (W)
(E)=electronic end stage of the ultrasound toothbrush (Uz)
(En)=unlocking groove
(F)=thin piezoelectric element, in particular a thin piezoelectric film
(H)=neck of the body of the carrier of the interchangeable brush head, i.e. the neck that is mechanically and electrically firmly connected with the handle (Hg) of the ultrasound toothbrush (Uz)
(Hg)=handle of the ultrasound toothbrush (Uz)
(K)=encapsulation of the electromechanical transducer (Pz), i.e. of a thin piezoelectric element and/or of a thin piezoelectric film
(Kk)=cable channel of the supply cables (L) and of the electromechanical transducer (Pz)
(L)=supply cable(s)
(M)=effective medium
(Mo)=coupling surface of the effective medium (M) and of the side (Bt-o) of the basic element that firmly carries the bristles (B), which side faces the effective medium (M)
(Pz)=electromechanical transducer
(Pz-o)=the surface of an electromechanical transducer (Pz), which surface emits ultrasound
(R)=engagement connection
(Rl)=engagement strips (Rl)
(Rn)=engagement grooves
(Sch)=sonic field
(V)=vibrator
(W)=thin wall (W)
(Wo)=lowest position, in terms of height, of the surface of the thin wall (W), which surface emits ultrasound, and, in general, the surface of the thin wall (W), which surface emits ultrasound
(Wm)=highest position, in terms of height, of the surface of the thin wall (W), which surface emits ultrasound, in relation to the bristles (B) used
(Uz)=ultrasound toothbrush
2=electrical power supply unit, rechargeable battery
3=control and electronics unit
4=operating switch, programming button
5=function display
6=display
7=holder of the charging station
8, 8a=electrical/electronic induction apparatus

The invention claimed is:
1. An interchangeable brush head with ultrasound action for ultrasound devices, the interchangeable brush head comprising:
a basic element having a first side, a plurality or great number of bristles affixed on the first side of the basic element, wherein the bristles form a bristle field, wherein the bristle field is situated in a spatial region of action of a sonic field, a thin wall comprising a thin wall ultrasound-emitting surface, wherein a wall thickness of the thin wall is equal to or less than a millimeter, at least one electromechanical transducer comprising a transducer ultrasound-emitting surface, the at least one electromechanical transducer being present in the sonic field, and emitting energy produced by ultrasound waves or by mechanical vibrations into an effective medium, via the transducer ultrasound-emitting surface and through the thin wall and the thin wall ultrasound-emitting surface, an encapsulation, wherein the thin wall is firmly connected with or coalesced with the encapsulation, without gaps, on a circumference side, in terms of material, wherein all corners and edges present on the encapsulation are rounded off, a carrier comprising a body, and a neck standing in axial connection with the body of the carrier, wherein the thin wall and the encapsulation comprise a hard material having a low damping coefficient, wherein the transducer ultrasound-emitting surface of the electromechanical transducer and the thin wall are inseparably and directly connected with or adhered to one another with a very thin layer of an adhesive having the low damping coefficient, wherein the thin wall ultrasound-emitting surface faces away from the electromechanical transducer and assumes a height position, in terms of height, in an individual case, within at least one of the bristle field, the sonic field, and the effective medium, between the first side of the basic element and a bristle half-height position, the bristle half-height position essentially corresponding to half a height of the bristles, in each instance, wherein the thin wall, the encapsulation, and the body of the carrier are connected, in terms of material, with the neck, and wherein the electromechanical transducer emits the energy produced by the ultrasound waves or by the mechanical vibrations in an axial direction that is parallel or essentially parallel to an expanse direction of the bristles.

2. The brush head according to claim 1, wherein the basic element is firmly connected, in terms of material, with the body of the carrier.

3. The brush head according to claim 1, further comprising a piezoelectric element, a cable channel, a covering, and supply cables situated in the cable channel, the supply cables being laid from a specific region along an elongated rear side of the neck and to solder points on the piezoelectric element, wherein the thin wall, the encapsulation, the basic element, and the body of the carrier are connected, in terms of material, with the neck and, in terms of production technology, form a one-part piece before application of the bristles, wherein the one-part piece comprises a hard material having the low damping coefficient, wherein the covering is situated above a rear side of the electromechanical transducer, wherein the covering covers the electromechanical transducer and the supply cables and protects the electromechanical transducer and the supply cables mechanically, electrically, and chemically, and wherein the covering continuously adapts to a cross-section progression of the body of the carrier and of the neck, in terms of a respective longitudinal expanse of the carrier and of the neck.

4. An ultrasound toothbrush comprising the brush head according to claim 1 and further comprising a piezoelectric element, a cable channel, a covering, supply cables situated in the cable channel, an accommodation recess, and a handle, the supply cables being laid from a specific region along an elongated rear side of the neck and to solder points on the piezoelectric element, wherein the encapsulation firmly encloses the electromechanical transducer, in terms of a height expanse of the electromechanical transducer, without gaps and, in terms of material, from all four sides of the electromechanical transducer, wherein the encapsulation carries the thin wall and forms a closure, in terms of height, wherein the accommodation recess is firmly connected with the encapsulation, in terms of material, wherein the neck is situated in an uninterrupted axial extension of the accommodation recess, wherein the thin wall, the encapsulation, and the accommodation recess are firmly connected, in terms of material, with the neck and are firmly connected with one another, in terms of material, as a whole, wherein the thin wall, the encapsulation, and the accommodation recess are produced as a one-part piece, in terms of production technology, before the bristles are applied, wherein the one-part piece comprises a hard material having the low damping coefficient, wherein an end of the neck axially faces away from the accommodation recess and is firmly and inseparably connected with the handle mechanically and electrically, wherein the covering is situated above a rear side of the electromechanical transducer, wherein the covering covers the electromechanical transducer and the supply cables, protecting the electromechanical transducer and the supply cables mechanically, electrically, and chemically, and wherein the covering continuously adapts to a cross-section progression of the body of the carrier and of the neck, in terms of a respective longitudinal expanse of the carrier and of the neck.

5. The brush head according to claim 1, wherein the body of the carrier comprises a bottom and walls that completely enclose the bottom on a circumference, essentially vertically, the bottom and the walls forming an accommodation recess that is open on one side, wherein the basic element comprises a separately produced and exchangeable replacement insert firmly carrying replacement bristles, wherein a body of the replacement insert fits into the accommodation recess, capable of engagement, and wherein an outer design form of the replacement insert is adapted to inner contours of the accommodation recess, for reciprocal engagement.

6. The brush head according to claim 1, wherein the body of the carrier comprises an accommodation recess having a wall and engagement grooves, the wall having inner sides, the engagement grooves being affixed on the inner sides of the wall, wherein the basic element comprises an interchangeable replacement insert carrying the bristles, the interchangeable replacement insert comprising engagement strips, wherein a stable but releasable engagement connection is formed between the interchangeable replacement insert and the accommodation recess, wherein the engagement grooves stand in engagement with the engagement strips, and wherein engagement and unlocking take place in a direction that is parallel or essentially parallel to a longitudinal expanse of the bristles.

7. The brush head according to claim 1, wherein the body of the carrier comprises an accommodation recess having an incision, an opening region, and a side wall, wherein the basic element comprises an interchangeable replacement insert carrying the bristles, the interchangeable replacement insert comprising a small-area unlocking groove built in at a height of the opening region of the accommodation recess, on an outside of the interchangeable replacement insert, wherein the incision is provided at a location of the side wall of the accommodation recess, the location spatially corresponding to the small-area unlocking groove, wherein via the incision and the small-area unlocking groove, unlocking can be undertaken via a lever effect, using a tip of a tool, wherein all the corners and edges are rounded off in an unlocking region, and wherein engagement and unlocking take place in a direction that is parallel or essentially parallel to a longitudinal expanse of the bristles.

8. An ultrasound toothbrush comprising the brush head according to claim 1 and a handle, the handle comprising a journal and metal pins projecting out of the journal, wherein an end region of the neck axially faces away from the bristle field and has an electrical and mechanical engagement connection, wherein the mechanical engagement connection is torque-proof and is formed via the journal of the handle and via a gap in a lower region of the neck, wherein the journal is polygonal in cross-section and the gap of the neck corresponds to the cross-section of the journal, wherein the neck comprises connecting sleeves, and wherein the electrical connection is produced via the metal pins and the connecting sleeves of the neck.

9. The brush head according to claim 1, further comprising a covering and a layer situated between a rear side of the electromechanical transducer and the covering, wherein the layer is suitable for a reflective effect of the ultrasound waves in a main direction of the ultrasound waves.

10. The brush head according to claim 1, wherein one or more substances that have a low damping coefficient for passing the ultrasound waves through are added to a material of the bristles, at least in part.

11. An ultrasound tooth brush comprising the brush head according to claim 1, a handle, and a vibrator affixed in the handle, wherein additional vibration operation takes place by the vibrator.

12. The brush head according to claim 1, wherein on the first side of the basic element at least one thin, piezoelectric element is applied, and wherein the thin piezoelectric element emits the ultrasound waves in an axial direction that is parallel or essentially parallel to the expanse direction of the bristles.

13. The brush head according to claim 1, wherein on the first side of the basic element at least one thin piezoelectric element is applied, wherein the at least one thin piezoelectric element is sheathed from all sides by the encapsulation so that the at least one thin piezoelectric element is firmly mechanically encapsulated in the encapsulation, wherein the thin piezoelectric element and an inner wall of the encapsulation are firmly and directly connected with or adhered to one another with a hard-to-rigid adhesive with the low damping coefficient, in a very thin layer of the hard-to-rigid adhesive, and wherein a surface of the encapsulation faces away from free bristle ends of the bristles and is directly connected with or adhered to the body of the carrier.

14. The brush head according to claim 1, wherein at least some bristle bundles of the bristles in a frontal view of the body of the carrier are inclined toward one another, in each instance.

15. The brush head according to claim 1, wherein the electromechanical transducer is placed in an immediate axial connecting region between an accommodation recess or the bristle field and an axially connecting region of the neck in the body of the carrier.

16. The brush head according to claim 1, wherein the entire body of the carrier comprises three brush head segments that are offset radially from one another, in each instance, and physically connected with one another such that a triple brush head is formed, wherein the entire body of the triple brush head includes the neck, the thin wall, connection elements, and the encapsulation and is built in one piece, at first without the bristles, specifically from a hard, amorphous plastic having the low damping coefficient, and wherein at least one brush head segment of the three brush head segments and/or an immediate vicinity of a brush head segment of the three brush head segments has the electromechanical transducer.

17. The brush head according to claim 1, wherein at least some bristle bundles on an end region of the bristle field that axially faces the neck are inclined toward the neck.

18. The brush head according to claim 1, wherein the carrier comprises one basic replacement insert placed radially centered, and three brush head segments on the one basic replacement insert, each of the three brush head segments being offset radially relative to one another and being physically connected with one another, wherein the body of the carrier is not interchangeable, includes an accommodation recess, the neck, the thin wall, and the encapsulation, and is built in one piece, specifically from a hard, amorphous plastic having the low damping coefficient, wherein the encapsulation is radially centered, wherein the electromechanical transducer is situated on an inside, in the encapsulation and/or in an immediate vicinity of the encapsulation, wherein each brush head segment of the three brush head segments comprises a respective bristle field, and wherein the three brush head segments are produced in one piece at first without the bristles.

19. The brush head according to claim 1, wherein the carrier comprises a basic replacement insert that is placed radially centered and does not have a bristle field, a first brush head segment on a left side of the basic replacement insert, and a second brush head segment on the right side of the basic replacement insert, the first brush head segment and the second brush head segment being offset radially from one another and being physically connected with one another, wherein the body of the carrier is not interchangeable, includes an accommodation recess, the neck, the thin wall, and the encapsulation, and is built in one piece, specifically from a hard, amorphous plastic having the low damping coefficient, wherein each of the first and the second brush head segments comprises a respective bristle field, wherein the electromechanical transducer is firmly housed in the encapsulation, wherein the carrier is not interchangeable, wherein in an engaged state the electromechanical transducer passes the energy of the ultrasound waves directly into the effective medium, and passes the energy through into the effective medium in at least one of a bristle field region and a sonic field region, out of a radially-geometrically center region of the carrier and out of a region of a central opening of the carrier, through the thin wall, and wherein at least some bristle bundles of the bristles intersect one another in a frontal view of the carrier, in a region of free bristle ends of the bristles.

20. A kit comprising the brush head according to claim 1 and a toothpaste, wherein the toothpaste has a lowest possible damping coefficient.

* * * * *